United States Patent [19]

Kreek et al.

[11] Patent Number: 4,785,000

[45] Date of Patent: Nov. 15, 1988

[54] METHOD OF TREATING PATIENTS SUFFERING FROM CHRONIC PAIN OR CHRONIC COUGH

[75] Inventors: Mary J. Kreek; Jack Fishman, both of New York, N.Y.

[73] Assignee: The Rockefeller University, New York, N.Y.

[21] Appl. No.: 121,784

[22] Filed: Nov. 16, 1987

Related U.S. Application Data

[62] Division of Ser. No. 875,560, Jun. 18, 1986.

[51] Int. Cl.4 ...................... A61K 31/22; A61K 31/44
[52] U.S. Cl. .................................... 514/282; 514/546
[58] Field of Search ................................ 514/282, 546

[56] References Cited

U.S. PATENT DOCUMENTS 3,896,226  7/1975  Lewinstein et al. ................ 514/282

OTHER PUBLICATIONS

Chem Abst. 78(1973)-47818y.

Primary Examiner—Stanley J. Friedman
Attorney, Agent, or Firm—Klauber & Jackson

[57] ABSTRACT

A method of treating patients in chronic pain or suffering from chronic cough over a prolonged period to provide systemic analgesia or central antitussive effect while simultaneously avoiding the onset of intestinal hypomotility. The method includes the oral administration to the patient of dosage units comprising in combination opioid analgesics or antitussives and selected opioid antagonists which are substantially devoid of systemic antagonist activity when administered orally.

9 Claims, No Drawings

METHOD OF TREATING PATIENTS SUFFERING FROM CHRONIC PAIN OR CHRONIC COUGH

This is a Division, of application Ser. No. 875,560, filed June 18, 1986.

BACKGROUND OF THE INVENTION

1. Field of the Invention

This invention relates to methods of treating patients suffering from chronic pain or chronic cough without provoking intestinal dysmotility.

2. Description of the Prior Art

The treatment of patients suffering from severe, chronic pain or chronic cough presents a number of serious clinical difficulties. Narcotic or opioid analgesic agents, such as morphine, methadone, codeine, meperidine and oxycodone are often administered to such patients, e.g. patients suffering from progressive cancer, pulmonary diseases, degenerative joint disease and chronic abdominal pain. However, apart from other undesirable side effects of long-term opioid administration, it is well known that chronic usage of long-acting opioid analgesics results in severe constipation and other symptoms of intestinal hypomotility. Although it is believed that tolerance to the constipating effects of chronic narcotic administration does eventually develop, it develops extremely slowly. Indeed, development of tolerance may be of little significance in the case of many elderly or terminal patients because of the limiting time factors or because doses of analgesic must normally be increased as tolerance develops to their analgesic effects.

The constipation and other symptoms of intestinal hypomotility caused by administration of opioid analgesics for chronic pain or cough not only create discomfort for the patient but may also complicate both the treatment program and the patient's underlying condition. In fact, chronic constipation may cause new health risks in and of itself, such as for cardiac patients and geriatric patients.

Traditional methods of relieving constipation in patients on long-term opioid analgesic regimens include the administration of a variety of laxatives, purgatives, stool softeners and lubricants, the regulation of diet, and the like. In some cases, the discomfort and potential danger of intestinal rupture created by constipation may become the limiting factor in the treatment of the pain and the doses of analgesic may have to be held constant at a given level or even reduced in an attempt to improve intestinal motility.

It has been proposed that certain opioid antagonists which have substantial systemic activity upon oral administration might be utilized to counteract the intestinal hypomotility provoked by long term administration of opioid agonists. Of course, in order to be of practical use, any such antagonists to be orally administered as adjuncts to analgesic or antitussive agents must not substantially interfere with the analgesic or antitussive effects of the opioid agonists administered to relieve pain or reduce cough. Thus, in U.S. Pat. No. 4,176,186, a family of compounds constituting quaternary derivatives of noroxymorphone are disclosed as being useful to prevent or relieve the intestinal motility-inhibiting side effects of narcotic analgesics without interfering with their analgesic activity.

The compounds disclosed in U.S. Pat. No. 4,176,186 and similar agents suggested in the prior art for alleviating the constipation problems of chronic pain patients suffer from a number of drawbacks. Although these substances do not cross the blood-brain barrier, and therefore do not substantially interfere with those analgesic effects of the opioid agents that are mediated through the brain, the antagonists suggested by the prior art may well interfere with analgesic activity mediated through the spinal cord, the peripheral sensory system, the pituitary gland and possibly the basal hypothalamus, all of which are believed to contain important opioid receptors. In addition, quaternary antagonists have low affinity for opioid receptors, including the gut receptors, and thus are not effective in counteracting narcotic induced-intestinal hypomotility. Furthermore, the prior art quaternary antagonist compounds have been found to have an unacceptably high degree of toxicity, making them particularly unsuitable for long term administration to chronic pain patients. No feasible or satisfactory method of treating chronic pain or cough patients utilizing the quaternary compounds has ever been disclosed.

In short, no safe, effective and practical means for alleviating the serious complication of intestinal hypomotility in chronic pain or cough patients undergoing opioid therapy has been heretofore developed, notwithstanding the long felt clinical need for such means.

SUMMARY OF THE INVENTION

Objects of the Invention

It is an object of the present invention to provide safe, effective methods of alleviating the symptoms of chronic pain or cough patients without provoking or aggravating disorders of intestinal motility.

It is another object of the present invention to provide methods as described above which are suitable for patients requiring long term opioid therapy.

A further object of the present invention is to provide methods as described above which comprise the administration of a pharmaceutical agent to chronic pain or cough patients concomitantly with their pain or cough medication to prevent and alleviate constipation and other symptoms of intestinal hypomotility.

Still another object of the present invention is to provide methods described above wherein the pharmaceutical agent administered concomitantly with the analgesic or antitussive medication does not significantly reduce or impair the latter's analgesic or antitussive activity.

Yet a further object of the present invention is to provide methods as described above wherein the agent administered as an adjunct to opioid analgesics can be administered orally and exhibits a low level of toxicity and low incidence of undesirable side effects.

Yet another object of the present invention is to provide methods described above wherein the adjunct agent comprises an opioid antagonist having little or no systemic bio-availability when taken by the oral route yet is effective in preventing and/or alleviating intestinal hypomotility.

Brief Description of the Invention

In keeping with these objects and others that will become apparent hereinafter, the present invention resides, briefly stated, in methods of treating chronic pain or cough patients, e.g. patients suffering from progressive cancer, pulmonary disease or progressive, degenerative joint disease, without provoking or aggravating disorders of intestinal motility such as constipation. The subject methods comprise the administration in combination or co-administration of an effective amount of an opioid analgesic or antitussive and an opioid antagonist which is systemically bio-available when administered by the parenteral route but is substantially non-bio-available when administered orally. Examples of suitable opioid analgesics include morphine, meperidine, oxycodone, methadone and the like. Among the most commonly used opioid antitussives are codeine and hydrocodone. Examples of suitable antagonists include naloxone, naloxone glucuronide and nalmefene glucuronide.

In accordance with the present invention, chronic pain or cough patients receive per os 1 to 2 dosage units comprising from about 1.5 to about 100 mg of opioid analgesic or antitussive and from about 1 to about 18 mg of suitable opioid antagonists (to be further defined below) 1 to 5 times daily. The two agents can be administered in combination in the form of tablets, capsules, caplets or prepared oral solutions, or can be dissolved or suspended together at time of administration in a suitable liquid vehicle, such as water, juice or other beverage. The two agents can also be co-administered in a non-simultaneous fashion, i.e., one of the agents is administered and, during the duration of its in vivo activity, the other agent is administered. tered.

DETAILED DESCRIPTION OF THE INVENTION

The present invention relates to methods of treating a patient in chronic pain or with chronic cough over a prolonged period to provide systemic analgesia or central antitussive effect while simultaneously preventing the onset of intestinal hypomotility or alleviating hypomotility which has resulted from use of narcotic alone. These methods comprise the oral administration in combination of pharmaceutically effective amounts of an opioid analgesic or antitussive and an opioid antagonist having little or no systemic bio-availability in active form and, hence, substantially devoid of systemic antagonist activity when administered orally.

Opioid agonists which may be used in the methods of the present invention include all known safe and effective opioid analgesics, both short and long-acting opioid analgesics, for example, morphine, meperidine, oxycodone, methadone, hydromorphone, codeine, hydrocodone and propoxyphene. Because the subject methods relate solely to the oral administration of the agonists and antagonists, the opioid analgesics or antitussives selected must have a high degree of oral activity and be safe for oral administration.

The opioid antagonists which are suitable for use in the methods of the present invention, hereinafter sometimes referred to as "suitable opioid antagonists", must have little to no systemic antagonist activity when administered orally. A low degree of oral systemic activity is a necessary feature of the opioid antagonists used in the present invention because when the antagonists are given in combination with the opioid agonists as taught herein, they have little value if they neutralize or substantially negate the analgesic activity of the opioid agonists.

The suitable opioid antagonists are generally of two types:

1. Agents which exhibit a high degree of antagonist activity when administered parenterally but are substantially (at least 95%) metabolized and lose systemic antagonist activity when administered orally. Such antagonists include, for example, naloxone (N-allyl-14-hydroxydihydronormorphinone).

2. Agents which are in the form of antagonist metabolites, e.g. naloxone glucuronide and nalmefene (6-methylene-6-desoxy-N-cyclopropylmethyl-14-hydroxydihydronormorphine) glucuronide, which are inactive metabolites of parenterally active antagonists.

It has been discovered that certain opioid antagonists which are poorly bio-available when administered orally do reach the gut in substantially unaltered form and are absorbed through the intestinal walls into the portal circulation, but then are quickly metabolized and deactivated in the liver —for example, naloxone is metabolized in the liver to naloxone glucuronide, which has little or no systemic antagonist activity. Yet, by reaching the gut opiate receptors, these antagonists are capable of blocking the hypomotility-causing effects of the opioid agonists on the gastrointestinal tract, and thus can prevent the onset, or alleviate the symptoms, of constipation in patients receiving long term narcotic analgesic therapy, while not interfering with or ablating the analgesic activity of the opioid agonists.

The glucuronide metabolites specified above also prevent the onset of constipation and/or reduce the severity of constipation in chronic pain patients receiving opioid analgesics, perhaps because they are deglucuronidated by bacterial activity or the activity of enzymes in the intestinal wall and reach the gut wall to some extent in the form of the antagonist bases, i.e., naloxone and nalmefene. Thus, it is believed that these metabolites act as pro-drugs when administered orally. As used herein the term "pro-drug" refers to substances which are inactive in vitro but are converted at least to some extent to a pharmaceutically active form in vivo.

In our co-pending application Ser. No. 680,230 filed Dec. 10, 1984 (continuation of Ser. No. 464,110 filed Feb. 4, 1983), we disclosed the utility of naloxone and other antagonist agents in relieving idiopathic or spontaneous constipation —i.e., constipation not caused by, for example, chronic administration of narcotic agonists. We emphasized on page 3 of that application that the invention therein disclosed did not relate to the use of opioid antagonists to neutralize the effect of opioid agonists such as narcotic drugs. The present invention relates to the use of specific opioid antagonists not to neutralize the systemic effects of narcotic agonists such as opioid analgesics, but only to counteact the gut level effects of the agonists on gastrointestinal motility while not otherwise blocking or interfering with any systemic agonist activity. Moreover, the methods of the present invention provide detailed dosage ranges and ratios for opioid analgesics and antitussives and suitable antagonists to provide a coherent method of acute or chronic treatment for patients with pain or cough which ensures adequate analgesia and antitussive activity while not compounding the patient's discomfort or aggravating the underlying illness with the complications of severe constipation.

In accordance with the novel methods of the present invention, patients suffering from chronic pain or cough, e.g., patients with progressive cancers, pulmonary disease, dengerative joint diseases, patients recovering from severe trauma and the like, receive one or two dosage units of opioid angonists and suitable antagonists 1 to 5 times daily. The opioid analgesics or antitussives utilized according to the present invention can be any short or long acting agents found to be safe and effective for long term use, such as, by way of example, morphine, meperidine, oxycodone, hydromorphone, methadone, codeine, hydrocodone and propoxyphene.

The dosage range for the opioid agents is from about 1.5 to about 100 mg per dosage unit, with 1 or 2 units being administered 1 to 5 times daily, yielding a daily dosage range of about 1.5 to about 1,000 mg of opioid agonist. The following are illustrative ranges for particular opioid analgesics:

TABLE 1

| Opioid Analgesics | Dosage Range Per Unit (mg) |
| --- | --- |
| morphine | 10 to 30 |
| meperidine | 50 to 150 |
| oxycodone | 5 to 15 |
| hydromorphone | 1.5 to 3 |
| methadone | 5 to 15 |
| codeine | 40 to 80 |
| propoxyphene | 40 to 80 |

Suitable opioid antagonists for use in the present invention are, as discussed above, those which have little or no systemic antagonist activity when administered orally yet are capable of acting on gut opiate receptors to block the dysmotility provoking effects of opioid agonists. Such suitable antagonists include those which are absorbed from the gastrointestinal tract in non-metabolized form to the extent of 5% or less, such as naloxone. In addition, metabolites of narcotic antagonists which have little or no systemic activity, e.g., naloxone glucuronide and nalmefene glucuronide, also have been found suitable for purposes of the present invention, probably because they act as pro-drugs. The key qualifications for the opioid antagonists suitable for use in the present invention are that they antagonize the adverse opioid effects on intestinal motility without significantly reducing the analgesic potency of the concomitantly administered opioid agonists.

In accordance with the present invention, chronic pain or cough patients receive a dosage amount of naloxone or other suitable antagonist together with each dosage amount of opioid analgesic, 1 to 5 times daily. Each dosage amount includes one or more dosage units comprising both pharmaceutical agents. The two agents can be combined in a fixed ratio in any pharmaceutically acceptable oral dosage form including, by way of example, capsules, tablets, caplets, syrups, elixirs and the like, with the addition of conventional carriers, binders, excipients, disintegration agents, lubricants, sweeteners and other known pharmaceutically acceptable additives. Alternatively, dosage amounts of opioid agonists and antagonists can be added in powdered form to a compatible beverage, such as fruit juice, for greater patient acceptability. The opioid agonist and suitable antagonist may also be co-administered to the patient in a non-simultaneous fashion with 1-5 dosage units of agonists and antagonists being separately administered to the patient.

The recommended dosage range for the narcotic antagonists suitable for use in the methods of the present invention is about 1 to about 18 mg per dosage unit. It has been found that a higher amount of antagonist, such as 12-18 mg per unit, is required with weaker agents such as codeine and propoxyphene, and a smaller amount of antagonist, such as 1-5 mg, per unit is required with stronger agonists such as morphine and meperidine. The following are typical unit and daily dosages of agonists and antagonists:

TABLE 2

| Opioid Analgesic | Representative Unit Dose (mg) | Representative Unit Dose Antagonist (Naloxone) | Typical Total Daily Dose of Agonist: Antagonist |
| --- | --- | --- | --- |
| morphine | 10 | 2 | 1-2 units qid |
| methadone | 10 | 2 | 1-2 units qid |
| meperidine | 50 | 2 | 1-2 units qid |
| oxycodone | 5 | 3 | 1-2 units qid |
| hydromorphone | 2.5 | 3 | 1-2 units qid |
| codeine | 60 | 12 | 2 units qid |
| propoxyphene | 65 | 18 | 2 units qid |

The novelty of the present methods of treating chronic pain or cough patients by providing effective analgesia and central antitussive effect without provoking or aggravating constipation and other symptoms of intestinal hypomotility is not detracted from by the fact that combinations of opioid agonists and antagonists (primarily naloxone) are disclosed in the prior art. None of these prior disclosures relates to the utility of opioid agonists and orally ineffective antagonists in combination for purposes disclosed herein, or in any other method of treatment where local antagonism of gut level opioid effects is desired.

For example, in U.S. Pat. No. 3,493,657 it is disclosed that naloxone is useful in conjunction with opiate alkaloids for ablating the respiratory depression caused by the opioids. But not only are the beneficial gastrointestinal effects of naloxone not disclosed in that patent, the combination formulations taught therein are only for parenteral use. Parenterally administered agonist-antagonist combinations would be useless in the methods of the present invention because the antagonist would seriously reduce the analgesic effect of the agonist while not improving intestinal motility as effectively as an orally administered preparation.

In U.S. Pat. No. 3,966,940, orally effective compositions are disclosed which comprise opioid analgesics and naloxone in combination. However, these combination formulations are disclosed as useful principally for the prevention of drug abuse because upon parenteral administration they do not produce analgesia, euphoria or physical dependence. This use of naloxone for the purpose of "adulterating" orally administered narcotic drugs to prevent parenteral abuse, such as by heroin and morphine addicts, is well known in the prior art. However, there is no prior disclosure in the patent or medical literature that such combination drugs would be useful in the treatment of chronic pain patients because of the oral effectiveness of naloxone in preventing narcotic induced constipation. Furthermore, it would not have occurred to skilled workers in the art to have utilized the prior art agonist-antagonist oral preparations to treat chronic pain patients where the possibility of parenteral abuse by the patients is not a significant concern.

Other combinations of opioid analgesics and naloxone suitable for prevention of parenteral abuse are disclosed in U.S. Pat. No. 4,582,835.

The following examples illustrate the methods of the present invention, but are in no way intended to indicate techniques, pharmaceutical agents, dosage forms or dosage amounts which must be utilized exclusively in order to come within the scope of the present invention.

The following examples represent titration studies which were performed on the subject patients. Opioid analgesics and antagonists were orally co-administered to the patients and the dosage ranges adjusted until the point where a significant increase in fecal passage was observed with increased fecal wet weight, and with no sign of narcotic withdrawal symptoms or recrudescence of pain. The dosage regimen discovered by titration to be optimal for achieving the foregoing results is referred to in the examples as the "optimal dosage regimen".

EXAMPLE 1

Patient No. 1 was a 42 year old female with a 9 year history of lower left quadrant abdominal pain, bloating and rectal bleeding, and a 5 year history of seizures. Her optimal dosage regimen was found to be 65 mg of propoxyphene and 18 mg of naloxone administered orally bid (twice daily).

EXAMPLE 2

Patient No. 2 was a 33 year old male with a 15 year history of narcotic addiction and a 5 year history of narcotic methadone maintenance treatment. Two years prior to admission, the patient had suffered a fall from a 30-foot ladder resulting in brain hemorrhaging, a fractured left femur and clavicle and secondary pain. The patient's optimal dosage regimen was found to be 100 mg of methadone, 5 mg of oxycodone and 8 mg of naloxone administered qd (once daily).

EXAMPLE 3

Patient No. 3 was a 59 year old female with a 13 year history of post-auto crash secondary spinal cord lesions, paraplegia, chronic pain and constipation. Her optimal dosage regimen was found to be 10 mg of methadone, 5 mg of oxycodone and 8 mg of naloxone administered tid (thrice daily).

EXAMPLE 4

Patient No. 4 was a 53 year old female with a 13 year history of post left mastectomy and right pneumonectomomy secondary pain. Her optimal dosage regimen was found to be 10 mg of oxycodone, administered 5 times daily as well as 10-12 mg of naloxone, 1-4 times daily.

EXAMPLE 5

Patient No. 5 was a 27 year old female with a 13 year history of intermittent small bowel obstruction diagnosed as pseduoobstruction and secondary chronic pain resulting in chronic narcotic dependency and methadone maintenance treatment. Her optimal dosage regimen was found to be 100 mg of methadone together with 4 mg of naloxone administered qd.

It will thus be seen that there are provided novel methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims.

1. A method of treating a patient in chronic pain or suffering from chronic cough over a prolonged period to provide systemic analgesia or central antitussive effect while simultaneously avoiding the onset of intestinal hypomotility, comprising the oral administration to the patient 1–5 times daily of 1–2 dosage units comprising from about 1.5 to about 100 mg of an opioid analgesic or antitussive selected from the group consisting of methadone and propoxyphene and from about 1 to about 18 mg of an opioid antagonist or antagonist pro-drug substantially devoid of systemic antagonist activity when administered orally.

2. A method according to claim 1 which comprises the use of an opioid antagonist absorbed into the bloodstream through the gastrointestinal tract in non-metabolized form to the extent of less than 5%.

3. A method according to claim 2 wherein said opioid antagonist is naloxone.

4. A method according to claim 1 which comprises the use of an antagonist pro-drug in the form of a metabolite of a parenterally active antagonist.

5. A method according to claim 4 wherein said antagonist pro-drug is selected from the group consisting of naloxone glucuronide and nalmefene glucuronide.

6. A method according to claim 1 wherein at least one dosage unit each of said analgesic or antitussive and antagonist or antagonist pro-drug is administered to the patient in combination in pharmaceutically acceptable oral dosage form.

7. A method according to claim 6 wherein said oral dosage form is selected from the group consisting of capsules, caplets, tablets, syrups and elixirs.

8. A method according to claim 1 wherein a dosage amount comprising at least one dosage unit each of analgesic or antitussive and antagonist or antagonist pro-drug is dissolved or suspended in a liquid beverage at the time of administration to the patient.

9. A method according to claims 6 or 8 wherein said dosage unit of antagonist includes from about 1 to about 18 mg of naloxone.

* * * * *